United States Patent
Sato et al.

(10) Patent No.: US 10,533,158 B2
(45) Date of Patent: Jan. 14, 2020

(54) CULTURED CELL SHEET, PRODUCTION METHOD THEREOF, AND APPLICATION METHOD THEREOF

(75) Inventors: Masato Sato, Yokohama (JP); Hideaki Sakai, Kawasaki (JP)

(73) Assignees: TOKAI UNIVERSITY EDUCATIONAL SYSTEM, Tokyo (JP); CELLSEED, INC., Kanagawa (JP)

( * ) Notice: Subject to any disclaimer, the term of this patent is extended or adjusted under 35 U.S.C. 154(b) by 255 days.

(21) Appl. No.: 11/885,246

(22) PCT Filed: Feb. 28, 2006

(86) PCT No.: PCT/JP2006/303759
§ 371 (c)(1),
(2), (4) Date: Aug. 28, 2007

(87) PCT Pub. No.: WO2006/093151
PCT Pub. Date: Sep. 8, 2006

(65) Prior Publication Data
US 2008/0226692 A1     Sep. 18, 2008

(30) Foreign Application Priority Data
Feb. 28, 2005 (JP) ................................. 2005-095995

(51) Int. Cl.
C12N 5/077 (2010.01)
A61L 27/38 (2006.01)
A61K 35/12 (2015.01)

(52) U.S. Cl.
CPC ........ *C12N 5/0655* (2013.01); *A61L 27/3817* (2013.01); *A61K 35/12* (2013.01); *A61L 2430/06* (2013.01); *C12N 2539/10* (2013.01)

(58) Field of Classification Search
CPC .............. C12N 5/0655; C12N 2539/10; A61L 27/3817; A61L 2430/06; A61K 35/12
See application file for complete search history.

(56) References Cited

U.S. PATENT DOCUMENTS

| | | | |
|---|---|---|---|
| 5,284,766 A | 2/1994 | Okano et al. | |
| 5,904,716 A | 5/1999 | Gendler | |
| 6,730,314 B2 | 5/2004 | Jeschke et al. | |
| 6,956,077 B1 | 10/2005 | Akiyama et al. | |
| 7,470,424 B2 | 12/2008 | Kataoka et al. | |
| 7,691,369 B2 | 4/2010 | Kataoka et al. | |
| 2002/0052044 A1 | 5/2002 | Jeschke et al. | |
| 2003/0036196 A1 | 2/2003 | Okano et al. | |
| 2003/0040113 A1* | 2/2003 | Mizuno et al. ................ | 435/395 |
| 2003/0077821 A1* | 4/2003 | Sah ....................... | A61K 35/32 435/366 |
| 2003/0228693 A1* | 12/2003 | Tsuzuki et al. ............... | 435/397 |
| 2004/0009566 A1* | 1/2004 | Okano et al. ................. | 435/174 |
| 2004/0028657 A1 | 2/2004 | Okano et al. | |
| 2004/0197907 A1 | 10/2004 | Kataoka et al. | |
| 2006/0153815 A1* | 7/2006 | Seyda et al. ................ | 424/93.7 |
| 2006/0234377 A1 | 10/2006 | Okano et al. | |
| 2006/0240400 A1 | 10/2006 | Yamato et al. | |
| 2006/0240552 A1 | 10/2006 | Yamato et al. | |
| 2007/0148137 A1 | 6/2007 | Okano et al. | |
| 2008/0118474 A1 | 5/2008 | Okano et al. | |
| 2008/0131476 A1 | 6/2008 | Kanzaki et al. | |
| 2008/0226692 A1 | 9/2008 | Sato et al. | |
| 2008/0289052 A1 | 11/2008 | Okano et al. | |
| 2009/0011504 A1 | 1/2009 | Kataoka et al. | |
| 2011/0229962 A1 | 9/2011 | Mizutani et al. | |
| 2012/0052524 A1 | 3/2012 | Kinooka et al. | |
| 2012/0107930 A1 | 5/2012 | Sasaki et al. | |
| 2012/0156781 A1 | 6/2012 | Takahashi et al. | |
| 2012/0210451 A1 | 8/2012 | Shimizu et al. | |
| 2014/0056814 A1 | 2/2014 | Okano et al. | |
| 2014/0056858 A1 | 2/2014 | Sugiyama et al. | |
| 2014/0072599 A1 | 3/2014 | Kinooka et al. | |

FOREIGN PATENT DOCUMENTS

| | | |
|---|---|---|
| CN | 101643760 | 2/2010 |
| EP | 0382214 | 8/1990 |
| EP | 0 552 380 | 7/1993 |
| EP | 0 739 631 | 10/1996 |

(Continued)

OTHER PUBLICATIONS

Kato et al. 1985. Sulfated Proteoglycan Synthesis by Confluent Cultures of Rabbit Costal Chondrocytes Grown in the Presence of Fibroblast Growth Factor. J. Cell Biol. 100:477-485.*
Temenoff et al. 2000. Review: tissue engineering for regeneration of articular cartilage. Biomaterials. 21:431-440.*
Ragan et al. 2000. Chondrocyte Extracellular Matrix Synthesis and Turnover Are Influenced by Static Compression in a New Alginate Disk Culture System Arch. Biochem. Biophy. vol. 383, No. 2, pp. 256-264.*
An et al. 2001. Regaining Chondrocyte Phenotype in Thermosensitive Gel Culture the Anatomical Record. 263:336-341.*
Konttinen et al. 1988. Synovial Fibroblasts. Scand. J. Rheumatol. Suppl. 76: 95-103.*
Yamato et al. 2001. Thermo-Responsive Culture Dishes Allow the Intact Harvest of Multilayered Keratinocyte Sheets without Dispase by Reducing TemperatureTissue Engineering. vol. 4, No. 7, p. 473-480.*

(Continued)

*Primary Examiner* — Taeyoon Kim
(74) *Attorney, Agent, or Firm* — Nixon & Vanderhye P.C.

(57) ABSTRACT

The problem to be solved by the present invention is to provide a cultured cell sheet that expresses phenotypes of the chondroid tissue. The problems can be solved by producing the cultured cell sheet in which cells are cultured on a surface of a cell cultureware that is coated with a temperature responsive polymer having an upper or lower critical solution temperature ranging from 0° C. to 80° C. in water, including steps of: adjusting the temperature of the culture medium to a temperature below the lower critical solution temperature or above the upper critical solution temperature; bringing the cultured cell sheet in close contact with the carrier; and detaching the cultured cell sheet together with the carrier.

12 Claims, 4 Drawing Sheets

(56) References Cited

FOREIGN PATENT DOCUMENTS

| | | | | |
|---|---|---|---|---|
| EP | 1312669 A1 * | 5/2003 | ........... | A61L 27/362 |
| EP | 1602383 | 12/2005 | | |
| EP | 1970439 | 9/2008 | | |
| JP | 9-23876 | 1/1997 | | |
| JP | 2004/261532 | 9/2004 | | |
| JP | 2004/261533 | 9/2004 | | |
| JP | 2005-261292 | 9/2005 | | |
| JP | 2007-080990 | 3/2007 | | |
| WO | 2004/069295 | 8/2004 | | |
| WO | 2004/073761 | 9/2004 | | |
| WO | 2005/011524 | 2/2005 | | |
| WO | 2005/012512 | 2/2005 | | |
| WO | 2006/093151 | 8/2006 | | |
| WO | 2007/148804 | 12/2007 | | |

OTHER PUBLICATIONS

Yang et al. Cell sheet engineering: Recreating tissues without biodegradable scaffolds. Biomaterials 26 (2005) 6415-6422.*

Useful Numbers for Cell Culture. ThermoFischer Scientific 2017. p. 1.*

Nevo et al. Adhesion Characteristics of Chondrocytes Cultured Separately and in Co-Cultures With Synovial Fibroblasts. Cell Biology international, vol. 17, No. 3, 1993 p. 255-273 (Year: 1993).*

International Search Report for PCT/JP2006/303759 dated Apr. 4, 2006.

Zipper et al., "Development of Chick Limb Bud Chondrocytes in Cell Culture: Morphologic and Oxidative Metabolic Observations" Clin. Orthop. Relat. Res., No. 155, pp. 186-195 (1981).

Kushida et al., "Decrease in culture temperature releases monolayer endothelial cell sheets together with deposited fibronectin matrix from temperature-responsive culture surfaces" J. Biomed. Mater Res., vol. 45, No. 4, pp. 355-362 (1999).

Sakai, "Nano Hyomen Kako Gijutsu no Saisei Iryo eno Tenkai" The Society of Fiber Science and Technology, Japan Yokoshu, vol. 59, No. 1, pp. 88-91 (2004).

Yamada et al., "Poly Isopropyl Acrylamide o Hyomen Grafting shita Saibo Baiyodoko kara no Kan Saibo no Atarashii Dacchaku Kaishuho" The Japanese Journal of Artificial Organs, vol. 21, No. 1, pp. 206-211 (1992).

Yamada et al., "Poly Isopropyl Acrylamide Grafting Hyomen ni Okeru Baiyo Saibo no Dacchaku Kiko" Polymer Preprints Japan, vol. 42, No. 3, p. 924 (1993).

Extended European Search Report for EP 06714889.0, six pages, dated Dec. 7, 2011.

Int'l Search Report for PCT/JP2012/054987, four pages (dated Apr. 2012).

Int'l Preliminary Report on Patentability for PCT/JP2012/054987, ten pages (dated Sep. 2013).

Extended European Search Report for EP 12752625.9, ten pages (dated Oct. 2014).

Araki et al, "Total glycome of ocular tissues and oral mucosal epithelial cell sheet" Journal of Japanese Biochemical Society, abstract only, 4T8a-7, 4P-0005 (Aug. 2011).

Miyamoto, "Synthesis of hyaluronic acid by corneal epithelial cells" Acta Medica Kinki University, vol. 23, No. 3, pp. 49-56 (1998).

Pincelli et al, "Keratinocytes stem cells: Friends and foes" Journal of Cellular Physiology, vol. 225, No. 2, pp. 310-315 (Nov. 2010).

Tammi et al, "Hyaluronate accumulation in human epidermis treated with retinoic acid in skin organ culture" Journal of Investigative Dermatology, vol. 92, No. 3, pp. 326-332 (1989).

Watanabe et al, "Development of transplantable genetically modified corneal epithelial cell sheets for gene therapy" Biomaterials, vol. 28, No. 4, pp. 745-749 (Feb. 2007).

Wu et al, "Enhancement of chondrogenesis of human adipose derived stem cells in a hyaluronan-enriched microenvironment" Biomaterials, vol. 31, No. 4, pp. 631-640 (Feb. 2010).

Japanese notification and English translation of the Notification of Reasons for Refusal for related JP Application No. 2014-078705, dated Jun. 26, 2015 (7 pages).

Fujii et al. *Biology of Bone and Cartilage—Development from Basic Research to Clinical Research*, partial translation of pp. 144-145 (Mar. 2002).

Jones et al. "Stem cell patterning and fate in human epidermis" *Cell*, 80:83-93 (1995).

Kierszenbaum & Tres *Histology and Cell Biology: An Introduction to Pathology, 3rd Ed.*, translation of Figure 1 to 3 (2012).

Kokubo et al. "Characterization of chondrocyte sheets prepared using a co-culture method with temperature-responsive culture inserts" *Journal of Tissue Engineering and Regenerative Medicine*, 10:486-495 (Jul. 2013).

Ohmasa et al. *Three-Dimensional Tissue Engineering—From Cell Culturing, Manipulation, and Organization to Quality Control and Decellularization*, partial translation of p. 213 (Feb. 2015).

BD Biosciences "BD Falcon cell culture inserts" et seq., pp. 32-45.

Abstract of Espinoza et al., J. Rheumatol., 21(8): 1507-11 (1994).

Fukaya et al., J. Exp. Med., 180: 225-232 (1996).

* cited by examiner

Layered Cell Sheets    Monolayer Cell Sheet

[FIG. 5]

Rt-PCR

CULTURED CELL SHEET, PRODUCTION METHOD THEREOF, AND APPLICATION METHOD THEREOF

This application is a U.S. national stage of International Patent Application No. PCT/JP2006/303759, filed 28 Feb. 2006, which designated the U.S. and claims priority benefit of JP 2005-095995, filed 28 Feb. 2005; the entire contents of each of which are hereby incorporated by reference.

TECHNICAL FIELD

The present invention relates to a cultured cell sheet, a production method and treatment method thereof for use in fields such as medical and biological osseous tissue and cartilage tissue.

BACKGROUND ART

Japan is becoming an aging society with the highest average life expectancy in the world. People are beginning to place more emphasis on living better, i.e., "quality of life" (QOL), rather than merely prolonging life. One area that is continuing to attract attention is motor dysfunction. Arthritis includes a wide variety of diseases that lead to motor dysfunction; and in the United States, more than 70 million patients visiting hospitals in 2002 complained of having symptoms of some type of arthritis or chronic arthropathia. Currently, one out every three adults has this disease. Moreover, this number is predicted to double by the year of 2020. As a medical problem it is second only to heart disease, and costs 86.2 billion dollars in medical expenses per year. Among visiting patients, more than 20 million people over the age of 45 have osteoarthritis, which is one of the most common forms of arthritis. In Japan, a large number of people are suffering from the onset of osteoarthritis, with a prevalence rate of 30% for people of age 45 to 65, and 63% to 85% for people over the age of 65. One million patients in Japan are suffering from osteoarthritis, and the number of new patients is expected to increase by 900,000 every year. Motor system diseases such as osteoarthritis, and the like, differ from diseases of organs, in that they are rarely life threatening. However, these diseases may limit movement in the limbs, and thereby remarkably decrease a person's QOL (quality of life). Such motor system diseases are predicted to increase dramatically in the future, due to an increasingly aging population, and personal and social problems resulting from these disorders will continue to be extremely important issues.

The majority of these types of motor system diseases are the result of inflammation or an injury to cartilage tissue or osseous tissue. Currently, in cases of a severe disease, artificial joints containing metals and a ultrahigh molecular weight polyethylene are employed as a treatment. However, an artificial joint wears out within about ten years after implantation; and various undesirable biological reactions can be caused by abrasive powders. Although, research is being conducted on improving abrasive resistance in order to solve these problems, limitations in abrasive resistance are expected. Also, treatments of cartilage or osseous tissue in which tissue regenerative engineering technique are utilized as new solutions are drawing attention. Such a treatment method includes a method in which cultured chondrocytes or osteocytes, and cartilage or osseous tissue produced thereof, are transplanted to the affected area of the patient.

In 1994, Brittberg, et al., reported a treatment method, whereby articular cartilage tissue was extracted from an unloaded portion of a joint, and isolated cartilage tissue cells were cultured and transplanted to full-thickness defect of the damaged cartilage (Brittberg, et al., New England Journal of Medicine, 331(14), 889 (1994)). Since approval of this treatment method by the FDA in 1997, it has been commercialized and performed in more than 20,000 cases around the world. A study of 219 cases over a period of 2 to 10 years confirm that performance of the treatment method from medium- and long-term standpoint was excellent, showing functional improvement in 89% of the cases (Peterson L., 6th Annual Meeting, American Academic Orthopedic Surgery (1998)). On the other hand, in 2002, cases of fatality due to bacterial infection after transplantation were reported, and a CDC investigation discovered 41 cases of postoperative infection, in Japan also. Information regarding such cases was provided by the Ministry of Health, Labor and Welfare, Health Service Bureau, to the Japanese Orthopaedic Association, which stated that such a problem had to be reaffirmed, and caution adopted in processing. Moreover, this method cannot be utilized in the treatment of osteoarthritis accompanying a broad range of partially defective and degenerative cartilage or osseous tissues, and therefore, improvement is needed.

In Japan also, cartilage tissue is reconstructed by tissue-engineering using isolated chondrocytes from articular cartilage of an unloaded portion or bone marrow-derived mesenchymal stem cells, and clinical applications directed to osteochondral full-thickness defects have begun. However, examples of the abovementioned clinical applications are related to traumatic osteochondral injuries and osteochondral dissecans, and this treatment is limitedly applied only to cases where a very small area of cartilage defect is present (Japanese Patent Application No. 2001-384446, Japanese Patent Application No. 2002-216561, Japanese Patent Application No. 2003-358118). Currently, since treatment performance in artificial joint replacement technique is stable, it would appear that no progress is being made in the treatment of osteoarthritis accompanying a broad range of degeneration or defect of cartilage or osseous tissues. Furthermore, since these techniques require a scaffold made of a protein, sugar, or artificial polymer, etc., other than one produced from cultured cells, the biological effects of these scaffolds are also raising new problems. Therefore, there is a definite need for the development of a technique which does not employ this type of scaffold.

On the other hand, Hunziker et al. intensively addressed fundamental research into a treatment for osteoarthritis, by focusing on the pathology of osteoarthritis in defects that do not extend to cartilage degeneration and subchondral bones, and conducting fundamental research employing a model for partial articular cartilage defects. In their research, they discovered that cartilage repair and regeneration was the central role of synovium cells, and not chondrocytes (Hunziker et al., The Journal of Bone and Joint Surgery, 78-A, 721 (1996)). However, since this technique is not necessarily practical, and has a limited range for potential treatments, the discussion in the Hunziker et al. does not directly provide for a treatment of oseteoarthritis. Therefore, there is a strong need for early establishment of this technique for treatment of osteochondral defects.

Conventionally, cell culture is conducted on a glass surface, or on the surface of a synthetic polymer compound along with a variety of surface processing. In order to achieve this, for example, various types of vessels made of polystyrene subjected to surface processing such as silicone coating, gamma irradiation, etc., are commonly used as vessels for cell culture. Cells that have been cultured and grown with these types of cell culture vessels, are detached and harvested from the surface of the vessel by a chemical agent treatment or a proteinase treatment such as trypsin. However, in cases where the cells are harvested by the abovementioned chemical agent treatment, some disadvantages have been pointed out: the treatment method is cumbersome and complicated; the potential for contamination by impurities is increasing; and examples of defects, in which cells are caused to degenerate or are damaged by the chemical treatment, and lose their original function.

Thus far, in order to overcome the abovementioned disadvantages, a number of techniques have been proposed by the present inventors. Especially, in Japanese Patent Application No. 2001-226141, a method for producing a cultured cell sheet which comprises steps of coating the surface of the cell cultureware with a temperature responsive polymer having a lower or upper critical solution temperature ranging from 0° C. to 80° C. in water, having the cultured cell layers multi-layered by way of a conventional method, as necessary, and detaching the cultured cell sheet only by changing the temperature of the cultureware. As a result of application of this method, a cultured cell sheet having sufficient strength without a scaffold, other than that produced from the cultured cells, can be produced. Furthermore, a thus obtained cultured cell sheet also retains basal membrane-like proteins, and also has improved adhesiveness to tissue, when compared with a cell sheet harvested using the above described dispase treatment. Moreover, PCT International Publication No. WO 02/08387 discloses a method for producing a cultured myocardial cell sheet, which comprises steps of culturing the cells of myocardial tissue on a cell cultureware having a cultureware surface coated or covered with a temperature responsive polymer, preparing a myocardium-like cell sheet, and subsequently, adjusting a temperature of the culture medium to a temperature greater than the upper critical solution temperature or less than the lower critical solution temperature, bringing the layered cultured cell sheet into close contact with a polymer membrane, detaching the cultured intact cell sheet together with the polymer membrane, and three-dimensionally structuring by a predetermined method. As a result of application of this method, a myocardium-like cell sheet and a three-dimensional structure were discovered to be constructed in vitro with reduced structural defects and with some of the functions of myocardial tissue.

However, none of these methods has been investigated with regard to application in technology aimed at regeneration therapy for cartilage and osseous tissue.

DISCLOSURE OF THE INVENTION

Problem(S) to be Solved

The present invention is intended to solve the abovementioned problems in conventional technology. Specifically, a purpose of the present invention is to provide a cultured cell sheet with excellent adhesiveness to osseous tissue or cartilage tissue. Moreover, a purpose of the present invention is to provide a method for manufacturing the cultured cell sheet and application method thereof.

Means for Solving the Problem(s)

The present inventors have conducted research and development, by investigating various aspects, in order to solve the abovementioned problems. As a result, it was discovered that a cultured cell sheet with excellent adhesiveness to the surface of osseous tissue or cartilage tissue was obtained by the steps of: culturing cells, such as cartilage tissue cells or osseous tissue cells, on a cell cultureware, the surface of which is coated with a temperature responsive polymer; and afterwards, adjusting a temperature of the culture medium to a temperature greater than the upper critical solution temperature or less than the lower critical solution temperature; bringing the cultured cell sheet in close contact with a carrier; and detaching the cultured cell sheet from the carrier while minimizing shrinkage. The present invention was completed based on the abovementioned knowledge.

Specifically, the present invention provides a cultured cell sheet in close contact with a carrier, which expresses phenotype of chondroid tissue and has superior adhesiveness to cartilage or osseous tissue The present invention provides a cultured cell sheet, which comprises a step of culturing at least one type of cell selected from the group consisting of: chondrocytes, chondroprogenitor cells, synovium derived cells, synovium derived stem cells, osteoblasts, mesenchymal stem cells, adipose derived cells and adipose derived stem cells, on a cell cultureware having a surface of the cultureware coated with a temperature responsive polymer having an upper or lower critical solution temperature ranging from 0° C. to 80° C. in water, and thereafter, comprising the steps of:

(1) adjusting the temperature of the culture medium to a temperature greater than the upper critical solution temperature or less than the lower critical solution temperature;
(2) bringing the cultured cell sheet in close contact with a carrier; and
(3) detaching the cultured cell sheet together with the carrier.

The cultured cell sheet obtained in the abovementioned manner demonstrates superior adhesiveness to the surface of cartilage or osseous tissue, and therefore, cultured cell sheets having superior adhesiveness, such as that of the present invention, are sometimes called, "highly adhesive cultured cell sheets".

Moreover, the present invention provides a highly adhesive cultured cell sheet for treating affected areas in which a portion or all of the cartilage or osseous tissue is damaged or impaired.

In addition, the present invention provides a treatment method which is conducted by transplanting the highly adhesive cultured cell sheet to the affected areas in which a portion or all of the cartilage or osseous tissue is damaged or impaired.

Effect of the Invention

The highly adhesive cultured cell sheet obtained by the present invention has extremely high adhesiveness to the surface of cartilage or osseous tissue. Therefore, the use of the cell sheet of the present invention enables to transplant target cells expressing phenotype of the cartilage or osseous tissue with a very high density, and enables to regenerate the tissue at an early stage. Moreover, transplantation of a layered cell sheet having three-dimensional polarity enables reconstruction of a target organ even more effective, and thus, broadens a scope of possible disease treatments. Consequently, the present invention is extremely useful in biological and medical fields, etc., such as cell engineering and medical engineering.

PREFERRED MODE FOR CARRYING OUT THE INVENTION

The present invention provides a cultured cell sheet in close contact with a support membrane used as a carrier, which express phenotype of chondroid tissue and has superior adhesiveness to cartilage tissue or osseous tissue. Suitable cells for producing the cultured cell sheet of the present invention may include any one type or combination of two or more types of cells selected from the group consisting of: chondrocytes, chondroprogenitor cells, synovium derived cells, synovium derived stem cells, osteoblasts, mesenchymal stem cells, adipose derived cells and adipose derived stem cells. However, the present invention is not strictly limited to the abovementioned types of cells. Furthermore, the abovementioned cells may be differentiated, for example, by a chondrogenic induction medium. However, the differentiation induction method of abovementioned cells is not strictly limited. In the present invention, the highly adhesive cultured cell refers to a sheet which is prepared by the steps of culturing each of the abovementioned types of cells as a single layer on the surface of the cultureware, and then, detaching the cell sheet from the cultureware. Thus obtained cell sheet has a lower side surface which is contacted to the cultureware at the time of culture, and an upper side surface on the opposite side thereof. If the cells are cultured on the cell cultureware, the surface of which is coated with a temperature responsive polymer having an upper or lower critical solution temperature ranging from 0° C. to 80° C. to in water indicated in the present invention, there will be an abundance of adhesive proteins produced on the lower side surface of the cell sheet at the time the cells are cultured.

The cultured cell sheet of the present invention, is one which is formed by culturing cells with high density. The cell density inside the cultured cell indicated in the present invention may vary depending on the cells that are cultured. However, a density of no less than 1000 cells/cm$^2$ is preferable, a density of no less than 3000 cells/cm$^2$ is more preferable, a density of no less than 5000 cells/cm$^2$ is even more preferable, and a density of no less than 7000 cells/cm$^2$ is the most preferable for effectively regenerating cartilage tissue and osseous tissue. Moreover, if the cell density inside the cultured cell sheet is no less than 1000 cells/cm$^2$, the cultured cells are flattened in many instances, specifically. In the case of chondrocytes where the degree is phenotypic expression is weak, the object of the present technology cannot be achieved.

One property of the cultured cell sheet of the present invention is that the cultured cell sheet expresses phenotype of chondroid tissue. In cases where the cell sheet expresses phenotype of chondroid tissue, it expresses hereditary characteristic such as SOX9 and HAS, or expresses differentiation characteristic such as collagen II relating to matrix formation.

The cultured cell sheet of the present invention may or may not include a scaffold other than that produced by the cultured cells, such as collagen, fibronectin, laminin, etc. However, it is not particularly limited. Moreover, it may be preferable not to include a scaffold, since the biological effects of the scaffold mentioned above may also becoming problems, and it is difficult to enhance the cell density via utilization of a scaffold.

The cultured cell sheet of the present invention is constructed of at least one type or a combination of two or more types of cells selected from the group consisting of: chondrocytes, chondroprogenitor cells, synovium derived cells, synovium derived stem cells, osteoblasts, mesenchymal stem cells, adipose derived cells and adipose derived stem cells. These cells are cells that are capable of expressing phenotype of the various types of chondroid tissue mentioned above.

The highly adhesive cultured cell sheet of the present invention adheres extremely well to the surface of living cartilage tissue or osseous tissue. This property is achieved by reducing the shrinkage of the cultured cell sheet that is detached from the surface of the cultureware. Moreover, a percentage of shrinkage of the cultured cell sheet when detached from the surface of the cultureware is preferably no more than 20%, more preferably no more than 10%, and even more preferably no more than 5%, in either of the lengthwise directions of the sheet. If the percentage of shrinkage is no less than 20%, the detached cell sheet becomes flaccid, and unable to adhere to living tissue well, even when attached to the living tissue. As a result, the detached cell sheet with no less than 20% shrinkage demonstrates the characteristics of the highly adhesive cell sheet of the present invention.

A method for preventing the cultured cell sheet from shrinking is not particularly limited in any way, and includes a method comprising the steps of bringing a ring-shaped carrier with a center portion cutout in close contact with the abovementioned cell sheets at the time of detaching the cultured cell sheet from the cultureware, and detaching the cell sheet with the abovementioned carrier.

The carrier that is used when detaching the highly adhesive cultured cell sheet has a structure for keeping the cell sheet of the present invention from shrinking, and a carrier such as that made of a polymer membrane, or a structure formed from a polymer membrane, or a metallic fixture, etc., may be used. For example, in cases where a polymer is used as the carrier material, biomacromolecules (such as hyaluronic acid, collagen, gelatin, fibrin, platelet-rich plasma, cellulose, other polysaccharides, bio-derived proteins polymers and such), polyvinyl alcohol, polyvinyl pyrrolidone, polyethylene glycol, polyvinylidene difluoride (PVDF), polypropylene, polyethylene, cellulose and derivatives thereof, papers, chitin, chitosan, urethane, etc., may be used as the specific material of the carrier. Specifically, in cases where the cultured cell sheet of the present invention is used in transplantation, by using a biomacromolecule such as hyaluronic acid, collagen, gelatin, fibrin, platelet-rich plasma, etc., the carrier can be left in the affected area where it has been transplanted, which is advantageous, in that the carrier and cell sheet in the affected area do not need to be separated at the time of transplantation.

In the case of the present invention the term "close contact" hereinafter refers to having the cell sheet in a state in which it does not slip or slide on the carrier, in order to prevent the cell sheet from shrinking at the boundary between the cell sheet and carrier, and therefore, it may be in close contact by being physically bonded, or it may be in close contact via the fluid (for example, the culture medium, and other isotonic solutions) existing between each of the cell sheet and the carrier.

The shape of the carrier is not specifically limited in any way. For example, when transplanting the highly adhesive cultured cell sheet obtained, if a cut out portion of the carrier which is the same size or larger than the transplantation site is utilized, greater convenience results since the cell sheet is only fixed to the portion surrounding the cutout portion, and only a cell sheet with a cut-out portion that fits the transplantation site can be transplanted.

Since the highly adhesive cultured cell sheet of the present invention is directly provided as a monolayered sheet, or is provided as a layered sheet, by layering multiple monolayered sheets, the thickness of the cell sheet can be controlled. Specifically, the thickness of the highly adhesive cultured cell sheet of the present invention is determined according to the number of sheets that have been layered.

Here, the layered sheet can be prepared by layering sheets consisting solely of the highly adhesive cultured cell sheet or may be prepared by combining the highly adhesive cultured cell sheet with a sheet of other cells. For example, a cell sheet includes, but is not limited to, one which is prepared by superimposing the abovementioned chondrocytic cell sheet and another chondrocytic cell sheet, or a cell sheet that is prepared by superimposing a cell sheet derived from cells other than those of the chondrocytic cell sheet (for example, a synovium derived cell sheet), etc., with the chondrocytic cell sheet. In such cases, if at least two different types of cells are employed, the different cells intercellularly interact with each other, and therefore, a cell sheet having the characteristic of even higher activity can be obtained. Furthermore, a position where the cell sheet is layered, the order of the layered cell sheets, and the number of the layered cell sheets are not particularly limited in any way. However, depending on the coated or covered tissue, the structure of the layered sheet may be varied, by employing a highly adhesive synovium derived cell sheet on the uppermost layer, and so on. In the case of cartilage tissue, it is preferred that the lowermost layer of the cell sheet is of chondrocytes or mesenchymal stem cells, or a combination thereof, and the uppermost layer comprises a synovium derived cell sheet; or that the lowermost and uppermost layers of the layered cell sheet are both of a synovium derived cell sheet. Furthermore, the number of the layered cell sheets is preferably no more than 10, more preferably no more than 8, and even more preferably no more than 4. The chondrocytes may also be viable even in an environment in which basic nutrients are not fully supplied. However, a cell sheet consisting of more than 10 layers of cell sheets is undesirable, since it is difficult to deliver oxygen and nutrients to the center portion of the layered cell sheets.

For example, the layered sheet of the present invention can be produced by employing a method, for example, but not limited to, the one described below:

(1) a method of superimposing the highly adhesive cultured cell sheet in close contact with the abovementioned carrier by the steps of attaching the first cell sheet in close contact with the carrier to the cell cultureware, and afterwards, removing the carrier off the first cell sheet by the addition of a culture medium, and layering the second cell sheet by attaching the second cell sheet in close contact with a carrier, and repeating the steps;

(2) a method of superimposing the highly adhesive cultured cell sheet in close contact with the abovementioned carrier by the steps of inverting the first cell sheet in close contact with the carrier, fixing the carrier side of the first cell sheet to the surface of the cell cultureware, attaching a second cell sheet to the cell sheet side of the first cell sheet, removing the carrier off the first cell sheet by adding culture medium afterwards, and repeating the steps by attaching another separate cell sheet;

(3) a method in which two cell sheets each in close contact with a carrier are brought into close contact with each other at the cell sheet side; and (4) a method in which the cell sheet in close contact with the carrier is fitted to an affected area of the individual, and after the cell sheet is attached to living tissue, removing the carrier, and overlaying another separate cell sheet on the affected area.

The highly adhesive cultured cell sheet of the present invention is characterized in that the basal membrane-like proteins between the cell and cultureware formed during the culture are not damaged by enzymes, such as proteinases like dispase, trypsin, etc. Therefore, in order to produce a cultured cell sheet with such a characteristic, the cell culture is preferably conducted on a surface of the cell cultureware coated with a temperature responsive polymer.

The temperature responsive polymer that is used to coat the cell cultureware has upper or lower critical solution temperature ranging from 0° C. to 80° C. in water, and more preferably a temperature ranging from 20° C. to 50° C. in water. An upper or lower critical solution temperature that exceeds 80° C. is not preferable, since cells may die. Furthermore, an upper or lower critical solution temperature that is lower than 0° C. is also not preferable, since it typically causes an extreme decrease in cellular growth rate or causes cell death.

The temperature responsive polymer to be used in the present invention may be either a homopolymer or a copolymer. Examples of such a polymer may include, for example, the polymer disclosed in Japanese Patent Publication No. H2-211865 (JP 2-211865 A). Specifically, for example, they may be obtained by polymerization or copolymerization of the monomer mentioned below. Monomers that can be used include, for example, (meth)acrylamide compound, N- (or N,N-di)alkyl substituted (meth)acrylamide derivative, or a vinyl ether derivative; in the case of a copolymer, at least two of these monomers may be selected and used. Moreover, those monomers may be copolymerized with other monomers, or polymers may be grafted together or copolymerized, or alternatively, mixtures of polymers and copolymers may be employed. If desired, the polymers may be crosslinked to an extent that does not impair their properties.

The cultureware that is to be covered with the temperature responsive polymer may be chosen from among the glass, modified glass, compounds such as polystyrene and poly (methyl methacrylate), and all other substances that can generally be shaped, as exemplified by polymer compounds other than those compounds, and ceramics.

The method of covering the cultureware with the temperature responsive polymer is not limited in any particular way but one may follow the methods described in JP 2-211865 A. Specifically, the coating operation can be achieved by either subjecting the cultureware and the abovementioned monomers or polymers to electron beam (EB) exposure, γ-ray irradiation, ultraviolet irradiation, plasma treatment, corona treatment or organic polymerization reaction or by means of physical adsorption as effected by application of coating solutions or the kneading step.

The coating of the temperature responsive polymer is suitably in the range of 0.5 to 5.0 $\mu g/cm^2$, preferably 1.0 to 4.0 $\mu g/cm^2$, and more preferably 1.2 to 3.5 $\mu g/cm^2$. If the coverage of the temperature responsive polymer is less than 0.5 $\mu g/cm^2$, the cells on the polymer will not easily detach even if they are given a stimulus and the operating efficiency is considerably lowered, which is not preferable. If, on the other hand, the coverage of the temperature responsive polymer is greater than 5.0 $\mu g/cm^2$, cells will not easily adhere to the covered area and adequate adhesion of the cells becomes difficult to achieve. The type of the cultureware of the present invention may include, for example, but is not particularly limited to, a dish, a multi-plate, a flask, a cell-insert, etc.

The composition of the culture medium for culturing the abovementioned cells of the present invention is not particularly limited in any way, and any conventionally used may be employed at the time the abovementioned cells are cultured. In the cases that chondrocytes, chondroprogenitor cells, synovium derived cells, synovium derived stem cells, osteoblasts, mesenchymal stem cells, adipose derived cells and the adipose derived stem cells are cultured, the culture medium may be prepared by, for example, supplementing an α-MEM culture medium, an F-12 culture medium, DMEM culture medium, or any mixture thereof, with 10% to 20% bovine serum, or optionally with 50 μg/ml of ascorbic acid 2-phosphate in addition to bovine serum.

Moreover, the culture medium may be a chondrocyte differentiation-inducing medium which includes factors for differentiating cultured cells into the chondrocytes, since the cells obtained thereby expresses phenotypes of chondrocytes to even greater degree, and therefore preferred. The chondrocyte differentiation-inducing medium can be produced by supplementing various factors for differentiating cultured cells into chondrocytes, (such as, but not limited to, TGF-β, IGF, IL, dexamethasone, BMP), to the abovementioned α-MEM culture medium, an F-12 culture medium, DMEM culture medium, or any mixture thereof, supplemented with 10% to 20% bovine serum, or optionally with 50 μg/ml of ascorbic acid 2-phosphate.

In addition, the highly adhesive property of the cultured cell sheet of the present invention to the surface of cartilage or osseous tissue is achieved under specific culture conditions. Specifically, the cultured cell sheet of the present invention is obtained by culture, after seeding cells to be cultured on the surface of the cultureware. It is demonstrated that the cultured cell sheet is prepared by harvesting the cell sheet after culturing the cells on the cultureware for no more than 14 days, preferably no more than 12 days, and more preferably no more than 10 days, from the date when the cultured cells become confluent on the cultureware. If culturing takes place more than 14 days after the confluent, the detached cultured cell sheet starts differentiation of the cells and results in the decreased cellular activity, and, therefore, it is not possible to obtain the cultured cell sheet of the present invention which should highly express the intended phenotype.

The temperature of the culture medium is not particularly limited, as long as the temperature is below the upper critical solution temperature, or above the lower critical solution temperature of the polymer that is coated onto the surface of the cultureware. However, it should be appreciated that a low temperature, where cultured cells can not proliferate, or high temperature region, where cultured cells undergo cell death, is of course unsuitable. Culture conditions other than temperature are not particularly limited, and conventional procedures may be followed. For example, a culture medium used may be a culture medium to which a serum such as common fetal bovine serum (FCS) has been supplemented, or a serum-free culture medium, to which no serum has been added.

When detaching and harvesting the cultured cells from the cultureware material by the method of the present invention, the highly adhesive cultured cell sheet in close contact with the carrier can be removed by the steps of bringing the cultured cell sheet in close with the carrier, adjusting the temperature of the cultureware attached to the cells to a temperature above the upper critical solution temperature, or below the lower critical solution temperature of the polymer coating the cultureware, increasing the hydrophilicity of polymer coating the surface of the cultureware, and detaching the cultured cell sheet in close contact with the carrier from the cultureware, due to weakening of the attachment between the cultureware and the cultured cell sheet. Moreover, the sheet may be detached either in the culture medium which is used to culture the cells, or in another isotonic solution, depending on the purpose.

In order to detach and harvest the highly adhesive cultured cell sheet at a high yield, a method in which the cell cultureware is lightly tapped and shaken, or a method in which the culture medium is agitated using a pipet, etc., may be used alone, or in combination. In addition, when required, cultured cells may be washed with isotonic solution, prior to detaching and harvesting.

The highly adhesive cultured cell sheet of the present invention, when harvested in the abovementioned manner, are not damaged by proteinases like dispase, trypsin, etc., from the time of culture to the time of detachment of the cell sheet. Therefore, the highly adhesive cell sheet which has been detached from the cultureware retains the intercellular desmosome structure, has only a few structural defects, and exhibits high strength. Furthermore, the basal membrane-like proteins of the sheet of the present invention between the cell and cultureware formed at the time of culture are not damaged by enzymes, thus providing superior adhesion to affected area at the time of transplantation, and allowing implementation of a very effective treatment to be possible. More specifically, in cases where conventional proteinases such as trypsin are used, the intercellular desmosomal structure and the basal membrane-like proteins between the cell and cultureware, etc., are not retained at all; and therefore, the cells are detached from the cultureware in a individually separated condition. Although it is commonly known that, among proteinases, dispase can allow for detachment with about 10% to 60% of the retained intercellular desmosomal structure, the basal membrane-like proteins between the cell and cultureware, etc., are almost completely damaged, and the cell sheet obtained has only low strength. However, the cell sheet of present invention keeps no less 80% of the desmosomal structure and basal membrane-like proteins intact, and therefore, provides the various effects described above.

The surface of the cartilage or osseous tissue of the present invention is not particularly limited. For example, the cartilage or osseous tissue generally includes articular cartilage, a meniscus, an intervertebral disc, costal cartilage, nasal septum, an auricular cartilage, etc. The cultured cell sheet of the present invention may be employed to treat an affected area, in which all or a portion of the cartilage tissue has been damaged or impaired, or to treat an affected area, in which a portion of the osseous tissue has been damaged or impaired. Specifically, the cultured cell sheet of the present invention is effective in the treatment of arthritis, arthropathia, a cartilaginous injury, a osteochondral injury, meniscus injury, or degeneration of an intervertebral disc, and particularly, as a novel treatment for osteoarthritis, which is difficult to be treated by the conventional therapy. The utilization of the highly adhesive cultured cell sheet of the present invention for the surface of the cartilage or osseous tissue may includes, for example, but not particularly limited to, a method in which the affected area is coated or covered with the highly adhesive cultured cell sheet of the present invention. In such cases, the cultured cell sheet may be cut to appropriately fit the size and shape of the affected area. In this way, the highly adhesive cultured cell sheet of the present invention is able to adhere extremely well to the surface of living cartilage and osseous tissue, which cannot be achieved by the prior art.

An application of the highly adhesive cultured cell sheet as shown in the present invention is effective, for example, but not particularly limited to, in treatments of osteoarthritis, arthritis, arthropathia, a cartilaginous injury, an osteochondral injury, meniscus injury, or degeneration of an intervertebral disc.

A method for fixing the highly adhesive cultured cell sheet to living tissue as demonstrated by the present invention is not particularly limited in any way, and therefore, the cell sheet may be sutured to living tissue, may be connected to living tissue with an adhesive agent capable of being used in vivo, or may only be attached to the affected area without using either of these means, in order to quickly graft the highly adhesive cultured cell sheet to living tissue as shown by the present invention.

A method for transplanting the highly adhesive cultured cell sheet of the present invention may include, but is not particularly limited to, for example, a method in which the highly adhesive cultured cell sheet is attached by incising the affected area, or a method in which the cell sheet is attached to the affected area with the use of an arthroscope. Specifically, the latter method is preferred because the treatment is less invasive to the patient.

In cases where the cultured cell sheet of the present invention is used in transplantation, the cell sheet is transplanted by removing the cell sheet off the carrier, after fitting the cell sheet to the affected area. The method for removing the cell sheet off the carrier include, for example, but not particularly limited to, a method of removing the cell sheet off the carrier by wetting the carrier in order to weaken the adhesiveness, or a method of cutting the cultured cell sheet using a cutting tool such as a scalpel, forceps, a laserbeam, a plasma wave, etc. For example, in cases where a cell sheet is in close contact with a carrier with a center portion cutout is employed, it is preferable to cut the cultured cell sheet to be transplanted with a laserbeam, or the like, along the border of the affected area, since it is possible to avoid attachment of the cultured cell sheet to an undesired area outside of the affected area.

The highly adhesive cultured cell sheet obtained by the method mentioned above is superior when compared with one obtained by conventional methods, due to the noninvasiveness of the cultured cell sheet at the time of detachment, and therefore, the clinical applications of the cartilage tissue or osseous tissue for transplantation, etc., are very promising. Especially, the highly adhesive cultured cell sheet of the present invention shows higher adhesiveness to living tissue than a conventional transplantation cell sheet, and grafts to living tissue very rapidly. Moreover, antigenic and infective problems can be solved due to the use of autologous cells.

From the perspective of cellular transplantation, researchers now focuses on research for transplanting the cultured cells with scaffolds after culturing cells three dimensionally within the scaffold, such as the collagen gel, and on research for transplanting the cultured cells with bioabsorbable membrane after culturing cells on the bioabsorbable membrane, etc. However, the cell density of the cultured cell sheet of the present invention is vastly superior to that of made of cells and the scaffolds or the bioabsorbable membrane. Further, the cell sheet of the present invention also has the advantage of having higher adhesiveness to target tissue than that of made of cells and the scaffolds or the bioabsorbable membrane since the cell sheet of the present invention excludes the bioabsorbable membrane and consists of the purified cells and the extracellular matrix. With respect to the fixation of, since the cultured cell sheet of the present invention is non-invasively harvested together with the extracellular matrix including the adhesion molecules secreted by the cultured cell sheet, which is transplanted, the cultured cell sheet has an advantage in early establishment on the surface of cartilage or osseous tissue to be transplanted when it is transplanted to the surface. Therefore, the present invention provides an extremely effective technology with improvements in the treatment efficiency of the affected area, and further alleviation of a burden on a patient.

EXAMPLES

Hereinafter, the present invention will be explained in further detail based on the following Examples, which are not intended to limit the scope of the present invention in any way.

Examples 1 and 2

To a commercial culture dish with a diameter of 3.5 cm (Falcon 3001, manufactured by Becton Dickinson Labware), 0.07 ml of the solution of N-isopropyl acrylamide monomer dissolved in isopropyl alcohol at a concentration of 53% (Example 1) or 54% (Example 2) was applied. The culture dish was exposed to electron beams at an intensity of 0.25 MGy, and the N-isopropyl acrylamide polymer (PIPAAm) was immobilized on a surface of the culture dish. After irradiation, the culture dish was washed with ion-exchanged water to remove a residual monomer and the PIPAAm that did not bind to the culture dish, was then dried inside a clean bench, and sterilized by ethylene oxide gas, to obtain a cell cultureware material coated with a temperature responsive polymer.

The amount of the temperature responsive polymer on the cultureware surface was measured. As a result, it was found that the cultureware' surface was coated with the temperature responsive polymer in an amount of 1.7 µg/cm$^2$ (Example 1), and 1.9 µg/cm$^2$ (Example 2), respectively. Articular cartilage was excised from a pig knee, treated with 0.4% (W/V) pronase for approximately 1 hour, and then 0.025% (W/V) collagenase for approximately 6 hours to obtain chondrocytes, which were seeded (7000 cells/cm$^2$) on the surface of each cell cultureware. DMEM/F12 culture medium supplemented with 20% bovine serum was used as the culture medium. The cells were cultured at 37° C., under 5% $CO_2$, resulting in adherence and proliferation normally on surface of each cell cultureware. Ten days after culture, the cultured cells were in a confluent state.

A carrier formed from polyvinylidene difluoride (PDVF) film having a diameter of 5 mm, with a center portion cutout having a diameter of 2 mm, was placed over the cells, the culture medium was gently aspirated, and each of the cell cultureware materials was incubated and cooled at 20° C. for 30 minutes, so that the cells on the cell cultureware material were detached along with the overlying carrier.

The obtained cell sheets had sufficient strength as a single sheet, with shrinkage of no more than 2%.

Figure 1:
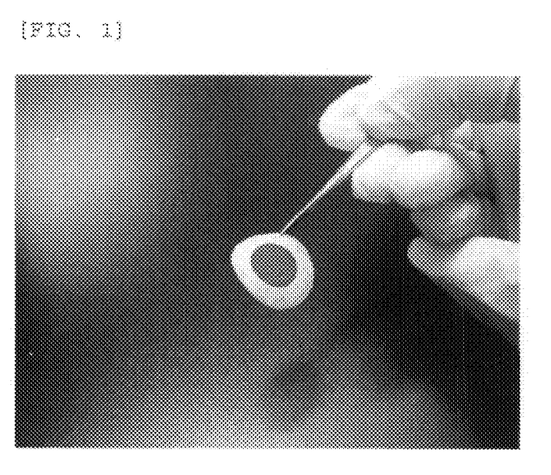
FIG. 1 shows a condition of a cultured cell sheet when detached using a carrier, 10 days after culture, as indicated in Example 2.

Moreover, although the "low-temperature treatment" in each of the abovementioned Examples was performed via incubation at 20° C. for 30 minutes, the "low-temperature treatment" of the present invention is not specifically limited to the conditions of the time and temperatures of abovementioned Examples. Preferred temperature conditions range from 0° C. to 30° C., and preferred treatment time range from 5 minutes to 1 hour for the "low-temperature treatment" of the present invention. FIG. 1 shows the condition of the cell sheet when detached using a carrier ten days after culture, in Example 2.

Example 3

The cell cultureware material was prepared by a similar method to that of Example 2, with the exception that, 0.07 ml of the solution of the N-isopropyl acrylamide monomer dissolved in isopropyl alcohol at a concentration of 55% was applied to the abovementioned commercial culture dish with a diameter of 3.5 cm (Falcon 3001, manufactured by Becton Dickinson Labware).

The amount of the temperature responsive polymer on the surface of the cultureware was measured. As a result, it was found that the cultureware's surface was coated with the polymer in an amount of 2.0 µg/cm². Articular cartilage was excised from a pig knee, treated with 0.4% (W/V) pronase for approximately 1 hour, and 0.025% (W/V) collagenase for approximately 6 hours to obtain chondrocytes, which were seeded (5000 cells/cm²) on the surface of the cell cultureware. DMEM/F12 culture medium supplemented with 20% bovine serum was used as the culture medium. The cells were cultured at 37° C., under 5% $CO_2$, resulting in adherence and proliferation normally on the surface of the cell cultureware. Ten days after culture, the cultured cells were in a confluent state.

On the cell sheet obtained adhered onto the surface of the cultureware material, the cultured cell sheet harvested by Example 2 was layered. Then, the carrier attached to the cultured cell sheet was removed, and a layered cultured cell sheet was obtained. At that time, the layered sheet was maintained as attached to the surface of the cell cultureware. Next, the layered cell sheet was detached from the cell cultureware. The layered cell sheet was detached from the cell cultureware by the method similar to that of Example 2.

Figure 2:
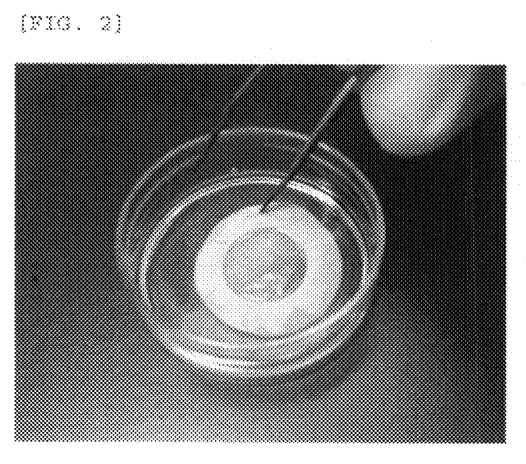
FIG. 2 is a photograph showing the condition of the cultured cell sheet when the cultured cell sheet indicated in Example 3 is layered.
Figure 3:
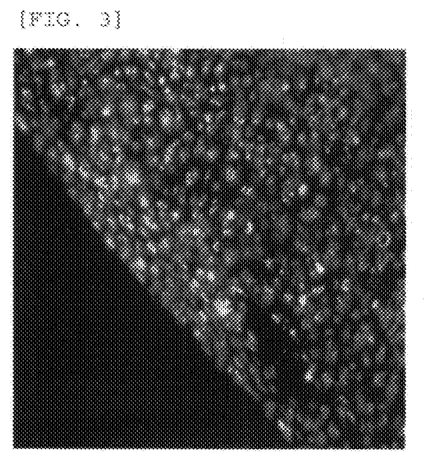
FIG. 3 is a photograph showing the results of PKH 26 staining of a portion of the layered cell sheet, indicated in Example 3.
Figure 4:
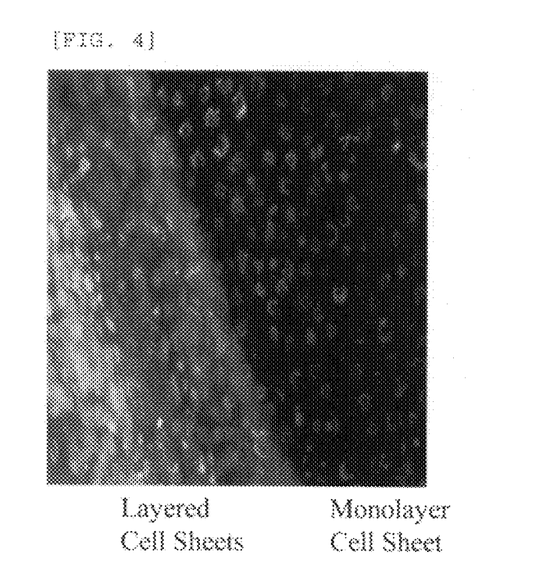
FIG. 4 is a photograph showing the results of PKH 26 staining of the portion of the layered cell sheet, and of a monolayer portion of the cell sheet, indicated in Example 3.

The obtained cell sheet had sufficient strength as a single sheet, with shrinkage of no more than 2%. FIG. 2 shows the layered cultured cell sheet obtained by Example 3. Moreover, the results of the PKH26 staining of the layered cultured cell sheet obtained by Example 3 using a standard method are shown in FIGS. 3 and 4. The upper right portion of the photograph of FIG. 4 is the monolayer area with only a few of the cells stained. On the other hand, since there are many stained cells in FIG. 3, and in the lower left portion of FIG. 4, it is demonstrated that the cell sheet obtained in this example was layered in these places.

Example 4 and Comparative Example 1

Figure 5:
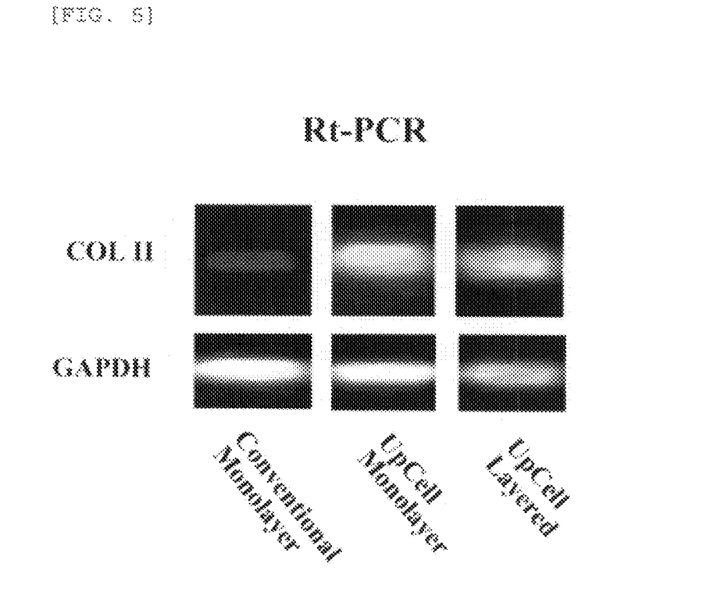
FIG. 5 is a diagram showing the analysis of the measured collagen II production using a Rt-PCR method, as described in Example 4.

The level of expression of the phenotype of the chondrocytes was examined using an Rt-PCR method by measuring the amount of chondrocyte specific collagen II production (COL II band intensity in FIG. 5). In the study, the monolayer type cultured cell sheet obtained by Example 2, the layered cultured cell sheet obtained by Example 3, and cells obtained by trypsin treatment from a conventional commercial cell cultureware without being coated with a temperature responsive polymer, were used.

The obtained results are shown in FIG. 5. The cells obtained by trypsin treatment expressed low lever of the collagen II production (the conventional cell cultureware, monolayer, in FIG. 5). On the other hand, the cells obtained in Example 2 (UpCell, monolayer, in FIG. 5) and Example 3 (UpCell, Layered, in FIG. 5) expressed a high concentration of the collagen II production. As a result, it is demonstrated that the cell sheet of the present invention has high activity.

Example 5

An osteoarthritis model was prepared by scratching approximately 1 mm on the surface of the articular cartilage of a pig knee using No. 40 sandpaper, to which the layered cultured cell sheet obtained by Example 3 was transplanted. Specifically, transplantation was completed by covering the exposed surface of the cartilage with the lower side of the cultured cell sheet of Example 3, and thereby protecting the surface of the wounded site.

Figure 6:
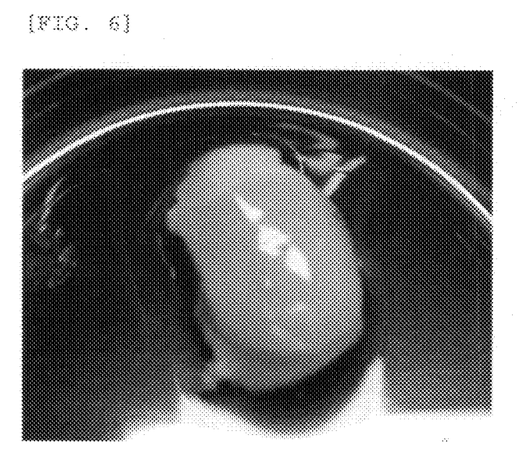
FIG. 6 is a diagram showing the condition of the layered cell sheet which is transplanted to the osteoarthritis model, as described in Example 5.
Figure 7:
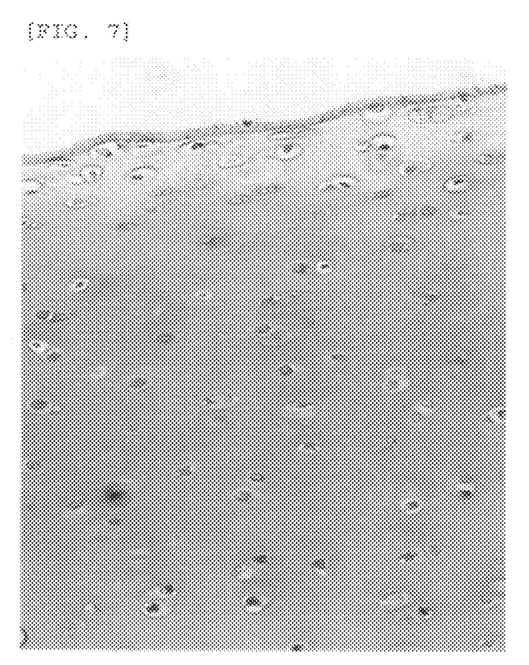
FIG. 7 is a diagram showing the adhesion condition of the layered cell sheet to the cartilage tissue at the transplantation site, as described in Example 5.

Three days after the operation, the transplantation site was sampled, which was treated by formalin fixation, EDTA decalcification, and paraffin embedding according to a standard method, and 5 µm serial sections were stained with Safranin-O, and the degree of adhesiveness to cartilage tissue was histologically determined. The condition at the time of transplantation is shown in FIG. 6. The results of the Safranin-O staining are shown in FIG. 7.

The applied layered cultured cell sheet was adhered to the cartilage surface of the pig osteoarthritis model, and was confirmed to suppress the discharge of proteoglycan from the extracellular matrix, etc., and to exhibit an anti-degenerative action. By transplanting the cultured cell sheet of the present invention, it was concluded that cartilage tissue can be reconstructed.

Comparative Example 2

An osteoarthritis model was prepared by scratching approximately 1 mm on the surface of the articular cartilage of a pig knee using No. 40 sandpaper, to which the layered cultured cell sheet was not transplanted.

Figure 8:
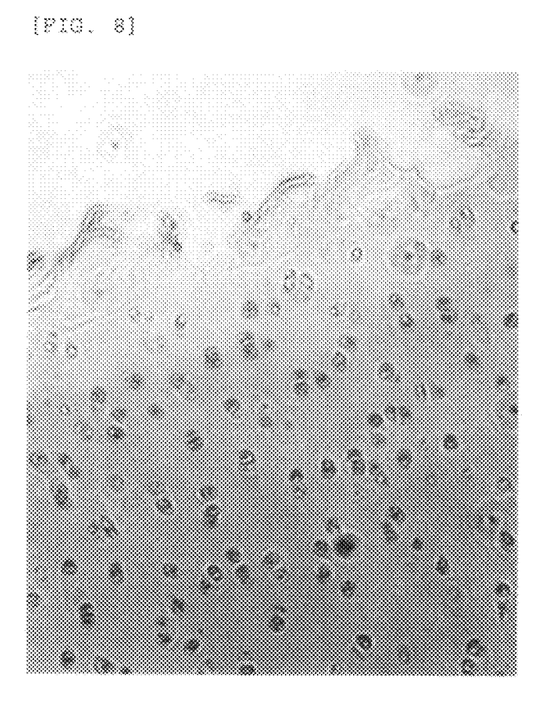
FIG. 8 is a diagram showing the condition of the layered cell sheet at the time when the cell sheet was not transplanted to the cartilage tissue, as described in Comparative Example 2.

Three days after the operation, the scratched site was sampled, which was treated by formalin fixation, EDTA decalcification, and paraffin embedding according using a standard method, and 5 µm serial sections were stained with Safranin-O, and the degree of adhesiveness to cartilage tissue was histologically determined. The results of the Safranin-O staining are shown in FIG. 8. It was confirmed that proteogylcan was being discharged from the extracellular matrix, etc., of the degenerative site that was scratched with sandpaper.

INDUSTRIAL APPLICABILITY

The highly adhesive cultured cell sheet obtained by the present invention has superior adhesiveness to a surface of cartilage or osseous tissue. Therefore, the use of the cell sheet of the present invention allows to transplant target cells with high density, and facilitates active reconstruction of cartilage or osseous tissue. Moreover, by transplanting a layered cell sheet which has three-dimensional polarity, an target organ can be reconstructed even more effective, and therefore, the clinical applications for arthritis, arthropathia, cartilage injuries, osteochondral injuries, meniscus injuries, degeneration of intervertebral discs, osteoarthritis, etc., are very promising. Consequently, the present invention is extremely useful in biological and medical fields, etc., such as cell engineering and medical engineering.

The invention claimed is:

1. A layered cultured cell sheet in close contact with a carrier,
   wherein there is a density of at least 1000 cells/cm' in the layered cultured cell sheet;
   wherein the layered cultured cell sheet does not include a scaffold other than that produced by the cultured cells, and comprises monolayered sheets comprising any one type or combination of two types of cells selected from the group consisting of chondrocytes and chondroprogenitor cells;
   wherein the cells present in the layered cultured cell sheet express phenotype of chondroid tissue and have adhesiveness to cartilage or osseous tissue;
   wherein the layered cultured cell sheet has a lower side surface contacted to a cell cultureware during culture, the layered cultured cell sheet has an upper side surface opposite the lower side surface, and the layered cultured cell sheet is detached from the cell cultureware after culture;
   wherein adhesive proteins are produced on the lower side surface when the cells are cultured;
   wherein the carrier contacts the layered cultured cell sheet on the upper side surface; and
   wherein the cell cultureware is coated with a temperature responsive polymer having an upper or lower critical solution temperature ranging from 0° C. to 80° C. in water, wherein the cell cultureware is a cell-insert, and wherein synovium derived cells or synovium derived stem cells are cultured in a medium outside of the cell-insert.

2. The layered cultured cell sheet according to claim 1, wherein the carrier is a gel-type or membrane-type carrier comprising any one material or combination of two or more types of materials selected from the group consisting of hyaluronic acid, collagen, gelatin, fibrin, platelet-rich plasma, polyvinyl alcohol, polyvinylidene difluoride (PVDF), polypropylene, polyethylene, cellulose and derivatives thereof, papers, chitin, chitosan, and urethane.

3. A method for producing a layered cultured cell sheet of claim 1, comprising culturing at least one type of cell which is selected from the group consisting of chondroncytes and chondroprogenitor cells on a cell cultureware, with synovium derived cells or synovium derived stem cells, wherein the cell cultureware has a surface coated with a temperature responsive polymer having an upper or lower critical solution temperature ranging from 0° C. to 80° C. in water, wherein the cell cultureware is a cell-insert, wherein a density of seeded cells per unit area of the cell cultureware is at least 1000 cells/cm', and wherein the synovium derived cells or synovium derived stem cells are cultured in a medium outside of the cell-insert; and, thereafter, further comprising:
   (1) adjusting the temperature of the culture medium to a temperature greater than the upper critical solution temperature or less than the lower critical solution temperature;
   (2) bringing the layered cultured cell sheet in close contact with a carrier; and
   (3) detaching from the cell cultureware, the layered cultured cell sheet together with the carrier.

4. The method for producing the layered cultured cell sheet according to claim 3, further comprising:
   (4) bringing the layered cultured cell sheet in close contact with the carrier obtained in (3), in close contact with the top of a separate cell sheet cultured on a separate cell cultureware, the surface of which is coated with the temperature responsive polymer having an upper or lower critical solution temperature ranging from 0° C. to 80° C. in water; and
   (5) repeating (1) to (3).

5. A treatment method, comprising transplanting the layered cultured cell sheet of claim 1 to an affected area in which a portion or all of the cartilage tissue, or a portion or all of the osseous tissue is damaged or impaired.

6. The treatment method according to claim 5, wherein the surface of cartilage or osseous tissue is coated or covered with the layered cultured cell sheet.

7. The treatment method according to claim 5, wherein before coating or covering the surface of cartilage or osseous tissue, the layered cultured cell sheet is cut in accordance with the size and shape of the affected area.

8. The treatment method according to claim 5, wherein before coating or covering the surface of the cartilage or osseous tissue, the layered cultured cell sheet is transported to the affected area using an arthroscope.

9. The treatment method according to claim 5, wherein the affected area to be treated is selected from the group consisting of the cartilage tissue portion of articulate cartilage, the cartilage tissue portion of a meniscus, the cartilage tissue portion of an intervertebral disc, the cartilage tissue portion of costal cartilage, the cartilage tissue portion of nasal septum, and the cartilage tissue portion of auricular cartilage.

10. The treatment method according to claim 5, wherein the portion or all of the cartilage tissue, or the portion or all of the osseous tissue is damaged by an arthritis, arthropathia, a cartilaginous injury, an osteochondral injury, a meniscus injury, or an intervertebral disc degeneration.

11. The treatment method according to claim 5, wherein the portion or all of the cartilage tissue, or the portion or all of the osseous tissue is damaged by an osteoarthritis.

12. The layered cultured cell sheet according to claim 1, wherein the layered cultured cell sheet is layered by superimposing the cell sheet.

* * * * *